United States Patent
Aebli et al.

(10) Patent No.: US 6,315,925 B1
(45) Date of Patent: Nov. 13, 2001

(54) NONYLATED DIPHENYLAMINES

(75) Inventors: Beat Michael Aebli, Basel; Samuel Evans, Marly; Sandor Gati, Allschwil, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/503,264

(22) Filed: Feb. 14, 2000

Related U.S. Application Data

(63) Continuation of application No. 09/090,651, filed on Jun. 4, 1998, now abandoned.

(30) Foreign Application Priority Data

Jun. 6, 1997 (CH) ..................................................... 1377/97

(51) Int. Cl.[7] ............................. C09K 15/16; C09K 15/18
(52) U.S. Cl. ......................... 252/401; 508/563; 564/409
(58) Field of Search ............................ 252/401; 508/563; 564/409

(56) References Cited

U.S. PATENT DOCUMENTS

| | | | |
|---|---|---|---|
| 2,776,994 | 1/1957 | Wolfe et al. | 260/576 |
| 2,943,112 | 6/1960 | Popoff et al. | 260/576 |
| 3,496,230 | 2/1970 | Kaplan | 260/576 |
| 4,739,121 | 4/1988 | Shaw | 564/409 |
| 4,824,601 * | 4/1989 | Franklin | 252/401 |
| 5,186,852 | 2/1993 | Ishida et al. | 252/401 |
| 5,672,752 * | 9/1997 | Lai et al. | 564/409 |
| 5,750,787 * | 5/1998 | Lai et al. | 564/409 |

FOREIGN PATENT DOCUMENTS

| | | |
|---|---|---|
| 0387979 | 9/1990 | (EP) . |
| 1508785 | 1/1967 | (FR) . |
| 1143250 | 2/1969 | (GB) . |

OTHER PUBLICATIONS

Webster's New Universal Unabridged Dictionary, Deluxe Second Edition, Abbreviations Commonly Used in Writing and Printing, pp. 100–101.
Derwent Abstract 1986–165254 [25] for JP 61097378.
Derwent Abstract 1983–726633 [31] for JP 5810826.

* cited by examiner

*Primary Examiner*—Jill Warden
*Assistant Examiner*—Monique T. Cole
(74) *Attorney, Agent, or Firm*—Kevin T. Mansfield

(57) ABSTRACT

The invention relates to a mixture of nonylated diphenylamines, especially dinonylated diphenylamines, and to a technically advantageous methodological process for the preparation of that mixture by using acid catalysts in small quantities. The mixture is used as an additive for stabilizing organic products that are subjected to oxidative, thermal and/or light-induced degradation.

11 Claims, No Drawings

NONYLATED DIPHENYLAMINES

This is a continuation of application Ser. No. 09/090,651 filed on Jun. 4, 1998, abandoned Feb. 16, 2000.

The invention relates to a mixture of nonylated diphenylamines, to a process for the preparation of that mixture and to the use thereof as an additive for stabilising organic products that are subjected to oxidative, thermal and/or light-induced degradation.

Additives are added to numerous organic products widely used in engineering, for example to lubricants, hydraulic fluids, metal-working fluids, fuels or polymers, to improve their performance properties. In particular, there is a need for additives that effectively inhibit the oxidative, thermal and/or light-induced degradation of those products and thereby considerably increase their useful life.

U.S. Pat. No. 2,943,112 describes anti-oxidants from the group of the alkylated diphenylamines that are prepared by reaction of diphenylamine with alkenes in the presence of mineral acids and large quantities of acid clays as catalysts. Alkylation of the diphenylamine with alkenes, for example nonene, results in mixtures of mono- and di-alkylated diphenylamine. In that process, relatively large quantities of the starting material, generally from 6 to 12% diphenylamine, are not reacted, which reduces the anti-oxidative efficacy of the alkylated diphenylamines, leads to the deposition of sludge and imparts undesirable toxic properties to the product. Reaction with additional alkenes is proposed as an alternative to the distillative separation of the starting material from the products.

U.S. Pat. No. 3,496,230 describes the preparation of a mixture of 80% dinonyidiphenylamine and 15% nonyldiphenylamine in the presence of Friedel-Crafts catalysts of the aluminium chloride type, but that mixture still has a diphenylamine content of 2% (see therein the information in Example 2). The preparation of that mixture is especially disadvantageous since it is contaminated by traces of chlorine, metal compounds and undesirable by-products, e.g. N-alkylated diphenylamines and diphenylamines alkylated in the 2- and 2'-positions, is black in colour and is very viscous.

European Patent Application No. 387 979 describes the reaction of diphenylamine with an eight-fold excess of tripropylene. That process is also disadvantageous since, in addition to the large excess of tripropylene, it is also carried out in the presence of large quantities of acid-activated clays.

The problem underlying the present invention is to prepare a mixture of nonylated diphenylamines that comprises as large as possible amounts of dinonyidiphenylamine, especially 4,4'-dinonyldiphenylamine, in addition to nonyldiphenylamine, e.g. 4-mononyidiphenylamine, and as small as possible amounts of undesirable by-products, e.g. N-alkylated diphenylamines and diphenylamines alkylated in the 2- and 2'-positions.

That problem is solved by a inventive process which comprises alkylating diphenylamine with an excess of nonene or a mixture of isomeric nonenes in the presence of from 2.0 to 25.0% by weight, based on diphenylamine, of an acid earth and in the absence of a free protonic acid.

The invention relates to a mixture of nonylated diphenylamines that has a content in a gas chromatogram (GLC, on-column method) of:

a) at least 68.0% by area dinonyldiphenylamine;
b) from 20.0 to 30.0% by area nonyidiphenylamine;
c) not more than 3.5% by area trinonyldiphenylamine; and
d) not more than 1.0% by area diphenylamine.

Preference is given to mixtures wherein the nonyl groups in the main component dinonyldiphenylamine and in the co-component nonyidiphenylamine are in the 4,4'-position and the 4-position, respectively, of the diphenylamine. Also preferred are mixtures wherein the nonyl groups are derived by reacting the diphenylamine with tripropylene.

In a preferred embodiment, the invention relates to a mixture comprising in a gas chromatogram:

a) from 70.0 to 75.0% by area dinonyldiphenylamine;
b) from 25.0 to 30.0% by area nonyidiphenylamine;
c) not more than 3.5% by area trinonyldiphenylamine and
d) not more than 1.0% by area diphenylamine.

In an especially preferred embodiment, the invention relates to a mixture comprising in a gas chromatogram:

a) from 70.0 to 75.0% by area dinonyldiphenylamine;
b) from 25.0 to 28.0% by area nonyldiphenylamine;
c) not more than 3.0% by area trinonyldiphenylamine and
d) not more than 0.8% by area diphenylamine.

The statement "at least 68.0% by area dinonyidiphenylamine" means preferably from 68.0 to 78.0% by area, especially from 70.0 to 75.0% by area, dinonyldiphenylamine.

In the preferred embodiments, the statements "not more than 3.5% by area trinonyldiphenylamine" means from 1.0 to 3.5% by area, preferably from 1.5 to 3.5% by area, also preferably from 2.0 to 3.5% by area and especially from 2.5 to 3.5% by area. The statement "not more than 3.0% by area trinonyldiphenylamine" means preferably from 1.0 to 3.0% by area, preferably from 1.5 to 3.0% by area, also preferably from 2.0 to 3.0% by area and especially from 2.5 to 3.0% by area, of that component.

The statement "not more than 1.0% by area diphenylamine" means preferably from 0.1 to 1.0% by area, especially from 0.3 to 0.8% by area, and the statement "not more than 0.8% by area diphenylamine" means preferably from 0.3 to 0.8% by area, especially from 0.3 to 0.6% by area, of that component in a gas chromatogram.

The invention also relates to the product of the inventive process obtainable by alkylation of diphenylamine with an excess of nonene or a mixture of isomeric nonenes in the presence of from 2.0 to 25.0% by weight, based on diphenylamine, of an acid earth and in the absence of a protonic acid.

The invention also relates to the product of that inventive process, which has a kinematic viscosity of <500 mm$^2$/sec at 40° C.

The invention further relates to the process for the preparation of a mixture of nonylated diphenylamines comprising in a gas chromatogram a) at least 68.0% by area dinonyidiphenylamine;
b) from 20.0 to 30.0% by area nonyidiphenylamine;
c) not more than 3.5% by area trinonyldiphenylamine; and
d) not more than 1.0% by area diphenylamine, which comprises alkylating diphenylamine with an excess of nonene or a mixture of isomeric nonenes in the presence of from 2.0 to 25.0% by weight, based on diphenylamine, of an acid earth and in the absence of a free protonic acid.

Preference is given to obtainable products for which from 5.0 to 20.0% by weight, especially from 5.0 to 10.0% by weight, of an acid earth is used in the process.

Suitable acid clays are, for example, active catalysts based on layered silicate, e.g. montmorillonites activated by mineral acids, such as sulfuric acid and/or hydrochloric acid, that preferably have a moisture content below 10%, especially below 5%, e.g. of the clays of the so-called Fuller type, e.g. types obtainable commercially under the names Fulcat®, e.g. types 20, 22 B and 40 (argillaceous earths activated by sulfuric acid), Fulmont® (Laporte Industries), e.g. types XMP-4, XMP-3, 700 C and 237, or acid earths of types K5 and K10 (activated by hydrochloric acid), KS and KSF (activated by sulfuric acid) or KSF0 (activated by hydrochloric acid and sulfuric acid) produced by Südchemie, and earths based on bentonite, e.g. products of the type Filtrol® or Retrol® (Engelhard Corp.).

The expression "absence of a free protonic acid" defines a feature of this process in which, in contrast to the process described in U.S. Pat. No. No. 2,943,112, no inorganic or organic acids are added to the reaction mixture.

Preference is given to obtainable products for which, as the nonene, tripropylene, especially a 4- to 10-fold molar excess of nonene, based on diphenylamine, is used in the process.

Special preference is given to obtainable products for which a from 4- to 8-fold, especially a 4- to 6-fold, molar excess of nonene, that is to say tripropylene, is used in the process.

The products of the process are obtained when the alkylation is carried out, for example, at a temperature range from 120° to 250° C., especially at a temperature of from 150° to 220° C.

The process can be carried out by introducing the starting materials and the acid clays, as the catalyst, into a suitable reaction vessel and by heating to the temperatures specified. In an alternative process variant, the tripropylene may be added to the reaction at a later point in time. The reaction is preferably carried out without the addition of organic solvents. The reaction time may be several hours, especially from 5 to 20 hours, before a diphenylamine content of less than 1% is reached, which can be ascertained by the taking of samples and analytical determination. The reaction is preferably carried out under elevated pressure, for example in an autoclave under a pressure of from 1 to 10 bar absolute pressure.

The acid clays used in the process can be removed from the reaction mixture by filtration, centrifugation or decanting, and are re-usable. In practice, they are used in an amount of from 5.0 to 20.0% by weight, especially from 5.0 to 10.0% by weight. If desired, the mixture is purified in customary manner, for example by distillation.

The process product has favourable viscosity characteristics. For example, in an Ubbelohde viscosimeter, low kinematic viscosities of <500 mm$^2$/sec at 40° C. are measured (ASTM D 445-94 method, micro-Ubbelohde 2.0–3.0 ml, Ubbelohde factor approx. 5). That value is lower than in the case of the products obtainable according to U.S. Pat. No. 3,496,230 by reaction with $AlCl_3$ which, with their intense coloration, are also less light-transmissive than the process products.

In the following Test Report, a comparison between the compositions that can be prepared according to Examples 2 and 4 of U.S. Pat. No. 3,496,230 and the composition according to the present invention demonstrates the distinct improvement in the properties:

Test Report

I. A mixture prepared according to Example 2 of U.S. Pat. No. 3,496,230 has the following composition and properties:

composition (see Example 1 below for methodology of the gas chromatography determination):
1.9% by area diphenylamine
25.1% by area monononyldiphenylamine
66.2% by area dinonyldiphenylamine
6.8% by area trinonyldiphenylamine black product having a light transmission of 6.5% at a wavelength of 425 nm contamination by chloride ions: 15 ppm (determined by X-ray fluorescence)

A mixture of 1% of that composition and 99% of a synthetic engine oil formulation based on a phosphorus content of 0.08% by weight is subjected to the test conditions of Test M 18, see Example 3 below. It has an induction period of 43 minutes compared with the induction period of 50 minutes that is obtained with the product according to Example 1.

II. A product prepared according to Example 4 of U.S. Pat. No. 3,496,230 has the following composition and properties:

composition (see Example 1 below for methodology of the gas chromatography determination):
1.1% by area diphenylamine
19.6% by area monononyldiphenylamine
71.6% by area dinonyldiphenylamine
7.5% by area trinonyldiphenylamine black product having a light transmission of 0.1% at a wavelength of 425 nm contamination by chloride ions: 15 ppm (determined by X-ray fluorescence)

A mixture of 1% of that composition and 99% of REOLUBE LPE 602 is subjected to the conditions of Test M 17, see Example 3 below. An induction period of 78 minutes is determined;

A mixture of 1% of that composition, 1.8% of a diesel catalyst made from a mixture of 25% of an iron naphthenate solution, 5% of a copper naphthenate solution, both from Strem Chem USA, and the remainder STANCO 150 mineral oil from Esso, and 97.2% REOLUBE LPE 602 is subjected to the test conditions of test M 17. An induction period of 73 minutes is determined;

A mixture of 1% of that composition, 0.5% nitropentane and 98.5% REOLUBE LPE 602 from FMC exhibits according to the loading test M 17 an induction period of 69 minutes. If a mixture of 1% of that composition and 99% of a synthetic engine oil formulation based on a phosphorus content of 0.08% is subjected to the test conditions of Test M 18, an induction period of 44 minutes is obtained.

III. The disadvantageous properties of the product prepared according to U.S. Pat. No. 3,496,230 which have been demonstrated are due to the distinctly higher trinonyldiphenylamine content. In order to provide evidence of the negative effect of trinonyldiphenylamine on the antioxidative action of a mixture of nonylated diphenylamine (mono- and di-nonyldiphenylamine), a product having a very high trinonyldiphenylamine content is prepared analogously to the process described in U.S. Pat. No. 3,496,230.

For that purpose, 42.3 g of diphenylamine are mixed with 5.33 g of aluminium chloride and 126.2 g of tripropylene, and the mixture is heated to reflux temperature and reacted for 2 hours. The unreacted tripropylene is thereafter removed by distillation. A further 70 g of fresh tripropylene are added. After a further 2 hours' reaction time, cooling to room temperature is carried out and the oily reaction mixture is extracted with 100 ml of water until the last extract has a pH value of 7. Thereafter, the unreacted tripropylene is removed by distillation under a vacuum and the reaction mixture is analysed by the gas chromatography method described in Example 1. The following composition is obtained:

0.1% by area diphenylamine
5.3% by area mononylnyldiphenylamine
72.5% by area dinonyldiphenylamine
22.1% by area trinonyidiphenylamine The product so prepared is analogously subjected to the test conditions of Test M 17. In that test, a considerably higher disadvantageous induction period of 56 minutes is measured. The product having the high trinonyidiphenylamine content is also subjected to the conditions of Test M 18. An induction period of 44 minutes is determined.

The mixtures according to the present invention have an outstanding anti-oxidative action, which can be demonstrated by favourable HPDSC values (High Pressure Differential Scanning Calorimetry), e.g. 79 min. for Test M 17 (sample at 200° C./SX, 10 bar $O_2$, 1% in REOLUBE LPE 602) or 50 min. for Test M 18 (sample at 200° C./SX, 8 bar $NO_x$, 1% in M251/0.08% P (Shell)). They can therefore be employed as additives in numerous organic products widely used in engineering, e.g. in lubricants, hydraulic fluids, metal-working fluids, fuels or polymers, and in the low molecular weight components on which the latter are based. The invention relates also to stabiliser-containing compositions comprising α) organic products subjected to oxidative, thermal and/or light-induced degradation and β), as stabiliser, at least one stabilising mixture comprising dinonyldiphenylamine as the main component as defined hereinbefore and prepared according to the process of the invention.

A particular class of organic products subjected to undesirable oxidative degradation for which the mixtures according to the present invention are valuable stabilisers is formed by lubricants and operational fluids based on mineral oil or synthetic lubricants or operational fluids, e.g. carboxylic acid ester derivatives, that can be used at temperatures of 200° C. and above.

The mixtures according to the present invention can be used in concentrations of from 0.05 to 10.0% by weight, based on the material to be stabilised. Preferred concentrations are from 0.05 to 5.0% by weight, especially from 0.1 to 2.5% by weight.

Mineral and synthetic lubricating oils, lubricating greases, hydraulic fluids and elastomers improved in that manner exhibit excellent anti-oxidation properties which become apparent through a great reduction in the ageing phenomena exhibited by the parts being protected. The mixtures described hereinbefore are especially advantageous in lubricating oils, in which they exhibit an excellent anti-oxidation and anti-corrosion action without the formation of acid or sludging.

Examples of synthetic lubricating oils include lubricants based on: a diester of a diprotonic acid with a monohydric alcohol, e.g. dioctyl sebacate or dinonyl adipate; a triester of trimethylolpropane with a monoprotonic acid or a mixture of such acids, e.g. trimethylolpropane tripelargonate or tricaprylate or mixtures thereof; a tetraester of pentaerythritol with a monoprotonic acid or a mixture of such acids, e.g. pentaerythritol tetracaprylate; or a complex ester of monoprotonic or diprotonic acids with polyhydric alcohols, e.g. a complex ester of trimethylolpropane with caprylic and sebacic acid or of a mixture thereof.

Other synthetic lubricants are familiar to the person skilled in the art and are described, for example, in "Schmiermittel Taschenbuch" (Hüthig-Verlag, Heidelberg, 1974). There are especially suitable, for example, poly-α-olefins, ester-based lubricants, phosphates, glycols, polyglycols and polyalkylene glycols.

Suitable elastomers are familiar to the person skilled in the art. Especially suitable are natural and synthetic rubbers, for example polymers of butadiene and copolymers thereof with styrene or acrylonitrile, and isoprene or chloroprene polymers.

Another class of polymers to be protected is formed by polycondensates, which can be protected from oxidative and light-induced degradation both in the state of the condensed macromolecular end product and in the state of the low molecular weight starting materials by the addition of the mixtures described hereinbefore. This class includes especially the polyurethanes, which can be stabilised by the addition of dinonyldiphenylamines to, for example, the polyols on which they are based.

The mixtures of the present invention can also be added to natural and synthetic organic substances that are pure monomeric compounds or mixtures thereof, for example mineral oils, animal or vegetable oils, waxes and fats, or oils, waxes and fats based on synthetic esters (e.g. phthalates, adipates, phosphates or trimellitates), and blends of synthetic esters with mineral oils in any desired weight ratios, as are used, for example, as spinning preparations, and aqueous emulsions thereof.

The mixtures of the present invention can be added to natural and synthetic emulsions of natural or synthetic rubbers, e.g. natural rubber latex or latexes of carboxylated styrene/butadiene copolymers.

The stabiliser-containing compositions may additionally comprise other co-additives which are added to improve the properties, e.g. further anti-oxidants, metal passivators, rust inhibitors, viscosity index improvers/melting point or pour point depressors, dispersants/detergents and wear protection additives or extreme pressure/anti-wear additives and friction improvers.

Examples of further anti-oxidants are:

1. Alkylated monophenols, e.g. 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, linear nonylphenols or nonylphenols branched in the side-chain, e.g. 2,6-dinonyl-4-methylphenol, 2,4-dimethyl-6-(1'-methylundec-1'-yl)-phenol, 2,4-dimethyl-6-(1'-methyl-heptadec-1'-yl)-phenol, 2,4-dimethyl-6-(1'-methyl-tridec-1'-yl)-phenol and mixtures thereof.

2. Alkylthiomethylphenols, e.g. 2,4-di-octylthiomethyl-6-tert-butylphenol, 2,4-di-octylthiomethyl-6-methylphenol, 2,4-di-octylthiomethyl-6-ethylphenol, 2,6-di-dodecylthiomethyl-4-nonylphenol.

3. Hydroquinones and alkylated hydroquinones, e.g. 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenyl-stearate, bis(3,5-di-tert-butyl-4-hydroxyphenyl)adipate.

4. Tocopherols, e.g. α-tocopherol, β-tocopherol, γ-tocopherol, δ-tocopherol and mixtures thereof (vitamin E).

5. Hydroxylated thiodiphenyl ethers, e.g. 2,2'-thio-bis(6-tert-butyl-4-methylphenol), 2,2'-thio-bis(4-octylphenol), 4,4'-thio-bis(6-tert-butyl-3-methylphenol), 4,4'-thio-bis(6-tert-butyl-2-methylphenol), 4,4'-thio-bis(3,6-di-sec-amylphenol), 4,4'-bis(2,6-dimethyl-4-hydroxyphenyl)-disulfide.

6. Alkylidene-bisphenols, e.g. 2,2'-methylene-bis(6-tert-butyl-4-methylphenol), 2,2'-methylene-bis(6-tert-butyl-4-ethylphenol), 2,2'-methylene-bis[4-methyl-6-(α-methylcyclohexyl)-phenol], 2,2'-methylene-bis(4-methyl-6-cyclohexylphenol), 2,2'-methylene-bis(6-nonyl-4-methylphenol), 2,2'-methylene-bis(4,6-di-tert-butylphenol), 2,2'-ethylidene-bis(4,6-di-tert-butylphenol), 2,2'-ethylidene-bis(6-tert-butyl-4-isobutylphenol), 2,2'-methylene-bis[6-(α-methylbenzyl)-4-nonylphenol], 2,2'-methylene-bis[6-(α,α-dimethylbenzyl)-4-nonylphenol], 4,4'-methylene-bis(2,6-di-tert-butylphenol), 4,4'-methylene-bis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercapto-butane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methyl-benzyl)-6-tert-butyl-4-methyl-phenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercapto-butane, 1,1,5,5-tetra(5-tert-butyl-4-hydroxy-2-methylphenyl)pentane.

7. O-, N- and S-benzyl compounds, e.g. 3,5,3',5'-tetra-tert-butyl-4,4'-dihydroxydibenzylether, octadecyl-4-hydroxy-3,5-dimethylbenzyl-mercaptoacetate, tridecyl-4-hydroxy-3,5-di-tert-butylbenzyl-mercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzyl-mercaptoacetate.

8. Hydroxybenzylated malonates, e.g. dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, di[4-(1,1,3,3-tetramethylbutyl)-phenyl]-2,2-bis(3,5-di-tert-butyl-4-hydroxybenzyl)malonate.

9. Hydroxybenzyl aromatic compounds, e.g. 1,3,5-tris(3,5-di-tert-butyl-4-hydroxybenzyl)-2,4,6-trimethylbenzene 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

10. Triazine compounds, e.g. 2,4-bis-octylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)-isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

11. Benzylphosphonates, e.g. dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, calcium salt of 3,5-di-tert-butyl-4-hydroxybenzyl-phosphonic acid monoethyl ester.

12. Acylaminophenols, e.g. 4-hydroxy-lauric acid anilide, 4-hydroxystearic acid anilide, N-(3,5-di-tert-butyl-4-hydroxyphenyl)-carbamic acid octyl ester.

13. Esters of β-(3,5-di-tert-butyl-4-hydroxyphenyl)-propionic acid with mono- or poly-hydric alcohols, e.g. with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis(hydroxyethyl)-oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

14. Esters of β-(5-tert-butyl-4-hydroxy-3-methylphenyl)-propionic acid with mono- or poly-hydric alcohols, e.g. with methanol, ethanol, n-octanol, iso-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis(hydroxyethyl)-oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

15. Esters of β-(3,5-dicyclohexyl-4-hydroxyphenyl)-propionic acid with mono- or poly-hydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis(hydroxyethyl)-oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

16. Esters of 3,5-di-tert-butyl-4-hydroxyphenylacetic acid with mono- or poly-hydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)-isocyanurate, N,N'-bis (hydroxyethyl)-oxalic acid diamide, 3-thiaundecanol, 3-thiapentadecanol, trimethylhexanediol, trimethylolpropane, 4-hydroxymethyl-1-phospha-2,6,7-trioxabicyclo[2.2.2]octane.

17. Amides of β-(3,5-di-tert-butyl-4-hydroxyphenyl)-propionic acid, e.g. N,N'-bis(3,5-di-tert-butyl-4-hydroxyphenylpropionyl)-hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)-hydrazine.

Examples of aminic anti-oxidants:

N,N'-di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di(naphth-2-yl)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di(4-methoxyphenyl)amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di[(2-methyl-phenyl)-amino]ethane, 1,2-di(phenylamino) propane, (o-tolyl)-biguanide, di[4-(1',3'-dimethyl-butyl)-phenyl]amine, tert-octylated N-phenyl-1-naphthylamine, mixture of mono- and di-alkylated tert-butyl-/tert-octyl-diphenylamines, mixture of mono- and di-alkylated dodecyldiphenylamines, mixture of mono- and di-alkylated isopropyl-/isohexyldiphenylamines, mixtures of mono- and di-alkylated tert-butyldiphenylamines, 2,3-dihydro-3,3-dimethyl-4H-1,4-benzothiazine, phenothiazine, mixture of mono- and di-alkylated tert-octyl-phenothiazines, N-allylphenothiazine, N,N,N',N'-tetraphenyl-1,4-diaminobut-2-ene, N,N-bis(2,2,6,6-tetramethyl-piperidin-4-yl)hexamethylenediamine, bis(2,2,6,6-tetramethylpiperidin-4-yl)sebacate, 2,2,6,6-tetramethylpiperidin-4-one, 2,2,6,6-tetramethylpiperidin-4-ol.

Examples of further anti-oxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, e.g. for copper:

a) Benzotriazoles and derivatives thereof, e.g. 4- or 5-alkylbenzotriazoles (e.g. tolutriazole) and derivatives thereof, 4,5,6,7-tetrahydrobenzotriazole, 5,5'-methylenebis-benzotriazole; Mannich bases of benzotriazole or tolutriazole such as 1-[di(2-ethylhexyl) aminomethyl]-tolutriazole and 1-[di(2-ethylhexyl) aminomethyl]-benzotriazole; alkoxyalkybenzotriazoles such as 1-(nonyloxymethyl)-benzotriazole, 1-(1-butoxyethyl)-benzotriazole and 1-(1-cyclohexyloxybutyl)-tolutriazole.

b) 1,2,4-Triazoles and derivatives thereof, e.g. 3-alkyl (or aryl)-1,2,4-triazoles, Mannich bases of 1,2,4-triazoles such as 1-[di(2-ethylhexyl)aminomethyl]-1,2,4-triazole; alkoxyalkyl-1,2,4-triazoles such as 1-(1-butoxyethyl)-1,2,4-triazole; acylated 3-amino-1,2,4-triazole.

c) Imidazole derivatives, e.g. 4,4'-methylenebis(2-undecyl-5-methyl)imidazole, bis[(N-methyl)-imidazol-2-yl]carbinol-octyl ether.

d) Sulfur-containing heterocyclic compounds, e.g. 2-mercaptobenzothiazole, 2,5-dimercapto-1,3,4-thiadiazole and derivatives thereof; 3,5-bis[di(2-ethylhexyl)amino-methyl]-1,3,4-thiadiazolin-2-one.

e) Amino compounds, e.g. salicylidene-propylenediamine, salicylaminoguanidine and salts thereof.

Examples of rust inhibitors:

a) Organic acids, their esters, metal salts, amine salts and anhydrides, e.g. alkyl- and alkenyl-succinic acids and their partial esters with alcohols, diols or hydroxycarboxylic acids, partial amides of alkyl- and alkenyl-succinic acids, 4-nonylphenoxyacetic acid, alkoxy- and alkoxyethoxy-carboxylic acids such as dodecyloxyacetic acid, dodecyloxy(ethoxy)-acetic acid and amine salts thereof, and N-oleoyl-sarcosine, sorbitan monooleate, lead naphthenate, alkenylsuccinic acid anhydrides, e.g. dodecenylsuccinic acid anhydride, 2-carboxymethyl-1-dodecyl-3-methylglycerol and amine salts thereof.

b) Nitrogen-containing compounds, e.g.:
   I. Primary, secondary or tertiary aliphatic or cycloaliphatic amines and amine salts of organic and inorganic acids, e.g. oil-soluble alkylammonium carboxylates, and 1-[N,N-bis(2-hydroxyethyl) amino]-3-(4-nonylphenoxy)propan-2-ol.
   II. Heterocyclic compounds, e.g.:
       Substituted imidazolines and oxazolines, 2-heptadecenyl-1-(2-hydroxyethyl)imidazoline.

c) Phosphorus-containing compounds, e.g.:
   Amine salts of phosphoric acid partial esters or phosphonic acid partial esters, zinc dialkyldithiophosphates.

d) Sulfur-containing compounds, e.g.:
   Barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, e.g:
   Glycerol monooleate, 1-(alkylphenoxy)-3-(2-hydroxyethyl)glycerols, 1-(alkylphenoxy)-3-(2,3-dihydroxypropyl)glycerols, 2-carboxyalkyl-1,3-dialkylglycerols.

Examples of viscosity index improvers:

Polyacrylates, polymethacrylates, vinylpyrrolidone/methacrylate copolymers, polyvinyloyrrolidones, polybutenes, olefin copolymers, styrene/acrylate copolymers, polyethers.

Examples of pour point depressors:
Polymethacrylate, alkylated naphthalene derivatives.
Examples of dispersants/surfactants:
Polybutenylsuccinic acid amides or imides, polybutenylphosphonic acid derivatives, basic magnesium, calcium and barium sulfonates, phenolates and salicylates.
Examples of wear protection additives:
Sulfur- and/or phosphorus- and/or halogen-containing compounds, such as sulfurized olefins and vegetable oils, zinc dialkyldithiophosphates, alkylated triphenylphosphates, tritolylphosphate, tricresylphosphate, chlorinated paraffins, alkyl and aryl di- and tri-sulfides, amine salts of mono- and di-alkylphosphates, amine salts of methylphosphonic acid, diethanolaminomethyltolyltriazole, di(2-ethylhexyl)aminomethyltolyltriazole, derivatives of 2,5-dimercapto- 1,3,4-thiadiazole, 3-[(bis-isopropyloxy-phosphinothioyl)thio]-propionic acid ethyl ester, triphenylthiophosphate (triphenylphosphorothioate), tris(alkylphenyl)phosphorothioates and mixtures thereof (e.g. tris(isononylphenyl)phosphorothioate), diphenyl-monononylphenyl-phosphorothioate, isobutylphenyl-diphenyl-phosphorothioate, dodecylamine salt of 3-hydroxy-1,3-thiaphosphetan-3-oxide, trithiophosphoric acid 5,5,5-tris[isooctyl acetate (2)], derivatives of 2-mercaptobenzothiazole such as 1-[N,N-bis(2-ethylhexyl)aminomethyl-2-mercapto-1H-1,3-benzothiazole, ethoxycarbonyl-5-octyl-dithiocarbamate.

The following Examples illustrate the invention; temperatures are given in degrees Celsius:

EXAMPLE 1

Reaction Under Elevated Pressure 1.1 Experimental Set-Up

The autoclave used is equipped with a reflux condenser having a water separator, electrical heating means, propeller stirrer, temperature-recording means and a device for taking samples. The reactions may be carried out under a nitrogen atmosphere or after previous evacuation of the autoclave.

1.2 Charge

The autoclave is filled with 40 g of diphenylamine and the latter is melted at 80°. 119.5 g of tripropylene (Exxon, U.S.A.) and 4.0 g of the catalyst FULCAT 22B (Laporte) are then added.

1.3 Performance of the Reaction

The autoclave is sealed and evacuated to a pressure of 20 mbar. With stirring, the autoclave is heated to 140° and maintained at that temperature for half an hour to remove the water from the acid catalyst earth. The beginning of the reaction (t=0) is set arbitrarily and the first sample is taken.

The autoclave is heated to 205–210° over a period of 45 minutes. At 210°, the pressure of the reaction mixture rises to 3.8 bar absolute pressure. The temperature is maintained at 210° for half an hour and is then reduced over a period of one hour to 156°. Thereafter, the reaction mixture is maintained at 156° for a further six hours.

1.4 Working-Up

The catalyst is allowed to settle in the reaction vessel over a period of one hour and the reaction mixture is then removed by sucking away the liquid above the catalyst clay deposited. The small amount of clay removed at the same time is separated off completely by filtration through a suction-filter having a pore size of approx. 1–3 μm. By vacuum distillation in a column, for example having 10 theoretical plates, at temperatures up to 270° and under a vacuum of 50 mbar the tripropylene starting material is removed from the reaction product. Upon increasing the temperature to 280–290° and at a further reduced pressure of 17 mbar, unreacted diphenylamine can be separated off. A sample (50% strength in toluene) has a light transmission of approx. 52.6% (UV-visible at 425 nm).

1.5 Gas Chromatograms

Gas chromatograms were made of the product obtainable according to Example 1, after removal of the tripropylene, and of a mixture obtainable according to Example 2 of French Pat. No. 1 508 785:

| components | Example 1 (% by area) | Example 2 U.S. Pat. No. 3,496,230 (% by area) |
|---|---|---|
| diphenylamine | 0.3 | 1.1/1.1 |
| monononyldiphenylamine | 25.6 | 25.4/25.4 |
| dinonyldiphenylamine | 71.5 | 67.4/67.7 |
| trinonyldiphenylamine | 2.6 | 6.1/5.8 |

1.51 Method: capillary—gas chromatography (GLC)

| | |
|---|---|
| gas chromatograph | Varian |
| injection method | direct injection "on column" |
| | Varian Auto Sampler 8035 |
| injection volume | 1 μl |
| column | fused silica |
| | length: 15 m, cross-section: 0.32 mm |
| stationary phase | silicone oil, DB-5, film thickness: 0.25 μm |
| detector | FID (sensitivity stage 10) |
| integrator | area under signal (peak); attenuation: 32 |
| integration period | 3–21 min. |
| carrier gases | He: 1.5 ml/min.; $N_2$: 30.0 ml/min.; $H_2$: 30.0 ml/min.; air: 300.0 ml/min. |
| temperatures | injector: 6 sec. at 95°, 100°/min. up to 300°, 21 min. at 300°; oven: 0 min. at 100°, 10°/min. up to 300°, 5 min. at 300°; detector: 300°. |
| measuring period | 28 min. |

EXAMPLE 2

Reaction Under Normal Pressure 2.1 Experimental Procedure

Instead of an autoclave being used, the reaction is carried out under a nitrogen atmosphere in a heatable 1000 ml glass reaction vessel having a water separator and reflux condenser. The reaction vessel is equipped in addition with a propeller stirrer, a thermometer, a sample-taking device and heat-transfer-medium heating means.

2.2 Charge

The reaction vessel is filled with 150 g of diphenylamine and the latter is melted at 80°. 111.9 g of tripropylene (Exxon, U.S.A.) and 15.0 g of the catalyst FULCAT 22B (Laporte) are then added.

2.3 Performance of the Reaction

The reaction mixture is stirred at 500 rev/min (revolutions per minute) and heated to boiling point to remove the water from the acid catalyst earth. The beginning of the reaction (t=0) is set arbitrarily and the first sample is taken. In the next two hours, the reaction temperature is increased to 175–180°. Thereafter, 336 g of nonene are metered in over a period of 10 hours. During that time, the reaction temperature falls to 155–158°. Thereafter, the reaction mixture is maintained under reflux conditions for a further 5 hours. Working-up is carried out analogously to Example 1.

After removal of the tripropylene, the mixture comprises in a gas chromatogram (see Example 1 for methodology):

0.7% by area diphenylamine
25.2% by area mononyldiphenylamine
71.5% by area dinonyidiphenylamine
2.6% by area trinonyidiphenylamine.

EXAMPLE 3

Use Example: Thermoanalytical Measuring Methodology

Method
HPDSC: High Pressure Differential Scanning Calorimetry

Apparatus
The instrument used is a DSC27HP apparatus of the METTLER TA-8000 series (Mettler-Toledo, CH-Greifensee)

Measuring Principle
DSC: heat flow to the sample measured as the difference of the heat flows to the sample crucible and the reference crucible. Heat adsorption by the sample indicates an endothermic reaction, e.g. a melting process.

Measuring Conditions (M 17)
A sample crucible containing 45 mg of a defined oil additive mixture is positioned together with an inert reference crucible, both made of steel, on the DSC sensor. The sealed cell is thoroughly flushed several times with the reaction gas, oxygen, and then placed under a pressure of 10 bar. At a heating rate of 50°/min, heating from room temperature to the reaction temperature of 200° is carried out.

Measuring Conditions (M 18)
A sample crucible containing 45 mg of a defined oil additive mixture is positioned together with an inert reference crucible, both made of steel, on the DSC sensor. The sealed cell is thoroughly flushed several times with the reaction gas, oxygen with 400 ppm nitric oxides, and then placed under a pressure of 8 bar. At a heating rate of 50°/min, heating from room temperature to the reaction temperature of 200° is carried out.

Evaluation
The induction period is used as the evaluation criterion. The induction period is the period in which the oxidation reaction visibly commences, formed by the point where the base line of the sensor intersects the tangent of the reaction signal. The TA-Station TAS810 used is based on the UNIX operating system, and Mettler Graphware TA3.00 is used as the evaluation software.

Results a) 1% of the product prepared according to Example 1 is mixed with the commercially obtainable oil REOLUBE LPE 602 from FMC, GB and the mixture is subjected to the test conditions of Test M 17. The measured induction period is 79 minutes.

b) 1% of the product prepared according to Example 1 and 1.8% of a diesel catalyst made from a mixture of 25% of an iron naphthenate solution, 5% of a copper naphthenate solution, both from Strem Chem, U.S.A., and the remainder STANCO 150 mineral oil from Esso is mixed with REOLUBE LPE 602 from FMC, GB I and likewise subjected to Test M 17. The induction period is 81 minutes.

c) A mixture of 1% of the product prepared according to Example 1, 0.5% nitropentane and 98.5% REOLUBE LPE 602 gives an induction period of 73 minutes under the test conditions of Test M 17.

d) If a mixture of 1% of the product prepared according to Example 1 and 99% of the synthetic engine oil formulation based on a phosphorus content of 0.08% is subjected to the test conditions of Test M 18 described above, an induction period of 50 minutes is obtained.

EXAMPLE 5

Analogously to the experimental set-up, working-up and analysis of Example 1, tests are carried out using different reaction procedures. The autoclave is charged in each test with 40 g of diphenylamine. Thereafter, the weight ml of tripropylene and m2 of the catalyst FUL-CAT 22B (Laporte) are added. The autoclave is evacuated to 20 mbar and heated to 140° to remove the water from the catalyst. The autoclave is then sealed and heated to the temperature T1 over a period of 15 minutes. Thereafter, the metering-in of dl grams of tripropylene per hour for a period of time t1 is commenced. Parallel thereto, the temperature is maintained at the temperature T1 for a period of time t2 and is then reduced over a period of time t3 to the final temperature T2. Thereafter, the reaction mixture is maintained at that temperature T2 with stirring, for a period of time t4. During the reaction, a maximum pressure of p1 bar absolute pressure builds up. At the end of the reaction, the reaction mixture is analysed by means of the gas chromatography method described in Example 1. The product composition without tripropylene data can be seen from Table 1. The abbreviations therein have the following meanings: DPA=diphenylamine, Mono= mononyldiphenylamine, Di=dinonyldiphenylamine and Tri=trinonyldiphenylamine. The percentages relate to percentages by area which can be determined by the gas chromatography method described in Example 1.

TABLE 1

| No. | m1 (g) | m2 (g) | T1 (° C.) | T2 (° C.) | p1 (bar) | d1 (g/h) | t1 (h) | t2 (h) | t3 (h) | t4 (h) | DPA (%) | Mono (%) | Di (%) | Tri (%) |
|---|---|---|---|---|---|---|---|---|---|---|---|---|---|---|
| 1 | 30 | 4 | 220 | 154 | 3.7 | 0.0 | 0.0 | 1.00 | 1.0 | 4.0 | 1.4 | 31.3 | 65.8 | 1.5 |
| 2 | 0 | 4 | 213 | 156 | 3.1 | 30.0 | 1.0 | 0.50 | 1.0 | 5.0 | 0.7 | 24.8 | 71.7 | 2.8 |
| 3 | 0 | 4 | 210 | 158 | 3.9 | 5.0 | 6.0 | 7.00 | 8.5 | 0.0 | 2.0 | 39.0 | 57.7 | 1.3 |
| 4 | 30 | 4 | 220 | 170 | 3.8 | 0.0 | 0.0 | 0.50 | 1.0 | 8.5 | 0.8 | 25.2 | 71.3 | 2.7 |
| 5 | 9 | 4 | 220 | 170 | 3.8 | 10.5 | 2.0 | 0.50 | 1.0 | 4.0 | 0.5 | 26.1 | 70.8 | 2.6 |

TABLE 1-continued

| No. | m1 (g) | m2 (g) | T1 (° C.) | T2 (° C.) | p1 (bar) | d1 (g/h) | t1 (h) | t2 (h) | t3 (h) | t4 (h) | DPA (%) | Mono (%) | Di (%) | Tri (%) |
|---|---|---|---|---|---|---|---|---|---|---|---|---|---|---|
| 6 | 0 | 4 | 220 | 160 | 1.5 | 15.0 | 2.0 | 0.25 | 2.0 | 4.0 | 0.3 | 24.1 | 72.8 | 2.8 |
| 7 | 0 | 2* | 220 | 160 | 1.5 | 7.5 | 4.0 | 0.25 | 2.0 | 4.0 | 0.3 | 24.4 | 72.5 | 2.8 |
| 8 | 0 | 2* | 220 | 160 | 1.5 | 7.5 | 4.0 | 0.25 | 2.0 | 6.0 | 0.7 | 26.0 | 70.7 | 2.6 |
| 9 | 0 | 2* | 220 | 160 | 1.5 | 7.5 | 4.0 | 0.25 | 2.0 | 6.0 | 0.8 | 26.5 | 70.2 | 2.5 |
| 10 | 0 | 2* | 220 | 160 | 1.5 | 7.5 | 4.0 | 0.25 | 2.0 | 6.0 | 0.9 | 27.0 | 69.8 | 2.3 |

*In tests 7–10 the catalyst from the preceding test is left in the reactor and only half of the usual amount of catalyst is added. In addition, in those tests, approximately 15 grams of reclaimed tripropylene from the preceding test is re-used and is supplemented by 15 grams of fresh tripropylene.

EXAMPLE 6

Analogously to the experimental set-up, working-up and analysis of Example 2, tests are carried out using different reaction procedures. The glass reactor of Example 2 is charged in each test with 150 g of diphenylamine. Thereafter, the weight m1 of tripropylene and m2 of the catalyst FULCAT 22B (Laporte) are added and the reaction mixture is heated to reflux temperature under normal pressure to remove the water from the catalyst. Thereafter, the reaction mixture is maintained under reflux for a period of time t2. Thereafter, the metering-in of d1 grams of tripropylene per hour for a period of time t1 is commenced, as a result of which the reaction temperature falls to a temperature T1 owing to the lower boiling temperature. The reaction mixture is finally maintained at reflux, with stirring, for t3 hours, as a result of which a final temperature T2 is reached. At the end of the reaction, the reaction mixture is analysed by means of the gas chromatography method described in Example 1. The product composition without tripropylene data can be seen from Table 2. The abbreviations therein have the following meanings: DPA=diphenylamine, Mono=mononoyldiphenylamine, Di=dinonyldiphenylamine and Tri=trinonyldiphenylamine. The percentages relate to percentages by area which can be determined by the gas chromatography method described in Example 1.

c) from 1.0 to 3.5% by area trinonyldiphenylamine; and
d) from 0.1 to 1.0% by area diphenylamine.
2. A mixture according to claim 1 consisting essentially of a content of:
a) from 70.0 to 75.0% by area dinonyldiphenylamine;
b) from 25.0 to 30.0% by area nonyldiphenylamine;
c) from 1.0 to 3.5% by area trinonyidiphenylamine; and
d) from 0.1 to 1.0% by area diphenylamine.
3. A mixture according to claim 1 consisting essentially of a content of:
a) from 70.0 to 75.0% by area dinonyldiphenylamine;
b) from 25.0 to 28.0% by area nonyldiphenylamine;
c) from 1.0 to 3.5% by area trinonyldiphenylamine; and
d) from 0.1 to 1.0% by area diphenylamine.
4. A mixture according to claim 1, wherein the nonyl groups in dinonyldiphenylamine and nonyldiphenylamine are in the 4,4'-position and 4-position, respectively, of the diphenylamine.
5. A mixture according to claim 1, wherein the nonyl groups are derived by reacting the diphenylamine with tripropylene.
6. A product according to claim 1 obtainable by alkylating diphenylamine with an excess of nonene or a mixture of isomeric nonenes in the presence of from 2.0 to 25.0% by weight, based on diphenylamine, of an acid clay and in the absence of inorganic or organic acids in the reaction mixture.

TABLE 2

| No. | m1 (g) | m2 (g) | T1 (° C.) | T2 (° C.) | T3 (° C.) | d1 (g/h) | t1 (h) | t2 (h) | t3 (h) | DPA (%) | Mono (%) | Di (%) | Tri (%) |
|---|---|---|---|---|---|---|---|---|---|---|---|---|---|
| 1 | 224 | 15.0 | 164 | 147 | 156 | 56 | 4.0 | 2.0 | 9.0 | 1.5 | 36.0 | 61.1 | 1.4 |
| 2 | 224 | 15.0 | 165 | 148 | 155 | 56 | 4.0 | 2.0 | 17.0 | 0.7 | 25.2 | 71.8 | 2.3 |
| 3 | 224 | 15.0 | 164 | 145 | 157 | 84 | 4.0 | 2.0 | 9.0 | 0.4 | 21.1 | 75.3 | 3.2 |
| 4 | 112 | 15.0 | 175 | 148 | 156 | 33.6 | 10.0 | 2.0 | 5.0 | 0.4 | 23.1 | 73.7 | 2.8 |
| 5 | 112 | 15.0 | 174 | 147 | 155 | 43** | 9.0 | 2.0 | 5.0 | 0.7 | 24.5 | 72.3 | 2.5 |
| 6 | 112 | 15.0 | 173 | 146 | 156 | 37 | 9.0 | 2.0 | 5.0 | 0.5 | 22.0 | 74.2 | 3.3 |
| 7 | 112 | 22.5 | 174 | 147 | 155 | 37** | 9.0 | 2.0 | 5.0 | 0.9 | 23.9 | 72.2 | 3.0 |
| 8 | 0 | 15.0 | 220 | 148 | 156 | 112 | 4.0 | 0.0 | 6.0 | 0.6 | 27.6 | 69.5 | 2.3 |
| 9 | 0 | 7.5* | 220 | 147 | 156 | 112 | 4.0 | 0.0 | 6.0 | 0.5 | 28.6 | 68.8 | 2.1 |
| 10 | 0 | 7.5* | 220 | 148 | 156 | 112 | 4.0 | 0.0 | 6.0 | 0.5 | 27.2 | 70.0 | 2.3 |
| 11 | 0 | 7.5* | 220 | 147 | 155 | 112 | 4.0 | 0.0 | 11.0 | 0.5 | 23.3 | 73.3 | 2.9 |

*In tests 9 to 11, the catalyst from the preceding test is left in the reactor and only half the amount of catalyst of test 7 is added in each case.
**In test 6 the reclaimed tripropylene from test 4, supplemented by fresh tripropylene, is used. In test 8, only reclaimed tripropylene from tests 6 and 7 is used.

What is claimed is:
1. A mixture of diphenylamines consisting in the gas chromatogram essentially of a content of
a) from 68.0% to 78.0% by area dinonyldiphenylamine;
b) from 20.0 to 30.0% by area nonyldiphenylamine;

7. A product according to claim 6, which has a kinematic viscosity of <500 mm$^2$/sec at 40° C.

8. A product according to claim 6, wherein from 5.0 to 10.0% by weight of an acid clay is used.

9. A product according to claim 6, wherein tripropylene is used as the nonene.

10. A process for the preparation of a mixture of nonylated diphenylamines consisting essentially of in a gas chromatogram a) from 68.0 to 78.0% by area dinonyldiphenylamine;
b) from 20.0 to 30.0% by area nonyldiphenylamine;
c) from 1.0 to 3.5% by area trinonyldiphenylamine;
d) and from 0.1 to 1.0% by area diphenylamine which comprises alkylating diphenylamine with an excess of nonene or a mixture of isomeric nonenes in the presence of from 2.0 to 25.0% by weight, based on diphenylamine, of an acid clay and in the absence of inorganic or organic acids in the reaction mixture.

11. A composition comprising

α) a lubricant or operational fluid subjected to oxidative, thermal and/or light-induced degradation and β) at least one mixture according to claim 1.

* * * * *